(12) United States Patent
Lee

(10) Patent No.: US 9,585,904 B2
(45) Date of Patent: Mar. 7, 2017

(54) METHOD FOR PRODUCING CULTURED ROOT OF PURPLE GINSENG

(76) Inventor: Hong Sik Lee, Jeju-do (KR)

(*) Notice: Subject to any disclaimer, the term of this patent is extended or adjusted under 35 U.S.C. 154(b) by 268 days.

(21) Appl. No.: 14/000,206

(22) PCT Filed: Jan. 19, 2012

(86) PCT No.: PCT/KR2012/000495
§ 371 (c)(1),
(2), (4) Date: Aug. 17, 2013

(87) PCT Pub. No.: WO2012/121484
PCT Pub. Date: Sep. 13, 2012

(65) Prior Publication Data
US 2013/0324486 A1    Dec. 5, 2013

(30) Foreign Application Priority Data

| Mar. 8, 2011 | (KR) | 10-2011-0020355 |
| Apr. 4, 2011 | (KR) | 10-2011-0030577 |
| Aug. 25, 2011 | (KR) | 10-2011-0085253 |
| Nov. 15, 2011 | (KR) | 10-2011-0119040 |

(51) Int. Cl.
*A61K 36/258* (2006.01)
*A61K 31/704* (2006.01)

(52) U.S. Cl.
CPC ........... *A61K 31/704* (2013.01); *A23L 5/13* (2016.08); *A23L 5/17* (2016.08); *A23L 19/00* (2016.08); *A23L 33/105* (2016.08); *A61K 36/258* (2013.01); *A23V 2002/00* (2013.01); *A61K 2236/00* (2013.01)

(58) Field of Classification Search
CPC ..................................... A61K 36/258
USPC ........................................ 424/728
See application file for complete search history.

(56) References Cited

U.S. PATENT DOCUMENTS

| 6,447,814 B1* | 9/2002 | Lee | A61K 36/232 |
| | | | 424/725 |
| 2005/0220903 A1* | 10/2005 | Lee | A61K 36/258 |
| | | | 424/728 |
| 2007/0224297 A1* | 9/2007 | Park | A61K 8/97 |
| | | | 424/728 |

FOREIGN PATENT DOCUMENTS

| CN | 101244104 A | | 8/2008 |
| CN | 101502548 | * | 8/2009 |
| CN | 101780128 | * | 7/2010 |
| JP | 11501322 A | | 2/1999 |
| KR | 20040103148 | * | 12/2004 |
| KR | 10-0506625 B1 | | 8/2005 |
| KR | 10-0545324 | * | 1/2006 |
| KR | 10-0602174 B1 | | 7/2006 |
| KR | 1020070077819 A | | 7/2007 |
| KR | 10-0837213 B1 | | 6/2008 |
| KR | 10-0876278 B1 | | 12/2008 |
| KR | 20100059306 | * | 6/2010 |
| KR | 20100098208 | * | 9/2010 |
| WO | 2008147141 A1 | | 12/2008 |
| WO | WO 2011013996 | * | 2/2011 |

OTHER PUBLICATIONS

Kim et al. J. Nat. Prod. 2000. vol. 63, pp. 1702-1704.*
Hwang et al. Food Sci. Biotechnol. 2010. vol. 19, No. 4, pp. 941-949.*
The Illinois Ginseng Conservation Law and Regulations. 2009. 4 pages. Obtained from https:dnr.state.il.us/law3/ginseng%20regulations.htm.*
Wang Yu Kim et al., Steaming of Ginseng at High Temperature Enhances Biological Activity, Journal of Natural Products, Oct. 21, 2000, pp. 1702-1704, vol. 63, American Chemical Society and American Society of Pharmacology, Internet publication.

* cited by examiner

*Primary Examiner* — Chris R Tate
(74) *Attorney, Agent, or Firm* — STIP Law Group, LLC

(57) ABSTRACT

The present invention relates to a novel method for processing a cultured root of purple wild ginseng for increasing saponin content and to the cultured root of the purple wild ginseng which is processed thereby. The present invention can provide the cultured root of wild ginseng having significantly higher content of a specific ginsenoside, and can increase the productivity and economic efficiency by simplifying the production process.

3 Claims, 4 Drawing Sheets

FIG. 2

Test Report

Life Science Research Center

| Issue No.: SeangCham 1102-082 | | | February 10, 2011 |
|---|---|---|---|
| Receipt No. | 12 - 1101 - 388 | Receipt Date | January 25, 2011 |
| Sample Name | Black Ginseng 2 | Preparation Date (Expiry Date) | - |
| Client(Manufacturing business or Institution name) | Choongam | Test division | For reference |
| Address (Contact details) | Choongam High School, San 9-1, Eungam-dong, Eunpyoung-gu, Seoul, Korea | | (02-308-6225) |

Test Results

| Test Item | Test Result | Notes |
|---|---|---|
| Ginsenoside Rg1 | 0.000 mg/g | |
| Ginsenoside Rf | 0.119 mg/g | |
| Ginsenoside Rg2 | 0.192 mg/g | |
| Ginsenoside Rh1 | 0.262 mg/g | |
| Ginsenoside Rg3 | 4.070 mg/g | |
| Ginsenoside Rh2 | 1.233 mg/g | |
| Crude saponin | 65.1 mg/g | |

February 10, 2011

Industry-University Collaboration Foundation of JOONGBU University

Food Sanitation Test Organization Designation No. 38 by the Korea Ministry of Food & Drug safety ☐ This result is limited to the submitted sample, and cannot be used for advertisement rather than a test purpose.

FIG. 3

Test Report

Life Science Research Center

Issue No. Seangcham 1106-533

Receipt No. 12-1106-237

| Product Name | | Black Ginseng | Manufacturing business (institution or number) | -- |
|---|---|---|---|---|
| Client | Business Name | Choongam | Name | LEE, Hong Sik |
| | Address | Choongam High School, San 9-1, Eungam-dong, Eunpyoung-gu, Seoul, Korea | | |
| Date of Receipt | | May 13, 2011 | Test expiry date | June 21, 2011 |
| Product Type | | -- | | |
| Test Purpose | | for reference | | |

Test Item and Result

| Test Item | Result | Notes |
|---|---|---|
| Ginsenoside Rg1 | 44.722 mg/kg | |
| Ginsenoside Rg2 | 104.280 mg/kg | |
| Ginsenoside Rg3 | 4768.102 mg/kg | |
| Ginsenoside Rh1 | 134.337 mg/kg | |
| Ginsenoside Rh2 | 3465.685 mg/kg | |
| Ginsenoside Rf | 46.651 mg/kg | |
| Crude saponin | 96.5 mg/g | |

Remarks: The content of the above test report is the test result of the materials submitted by the client and the Foundation is not liable for all matters which may be caused by the use rather than a test purpose.

June 21, 2011

Industry-University Collaboration Foundation of JOONGBU University

FIG. 4

Test Report

Life Science Research Center

Issue No. Seangcham 1108-380  
Receipt No. 12-1108-124

| Product Name | Back Ginseng (high temperature) | Manufacturing business (institution or member) | -- |
|---|---|---|---|
| Client — Business Name | Choongam | Name | LEE, Hong Sik |
| Client — Address | Choongam High School, San 9-1, Eungam-dong, Eunpyoung-gu, Seoul, Korea | | |
| Date of Receipt | August 4, 2011 | Inspection expiry date | August 12, 2011 |
| Product Type | -- | | |
| Test Purpose | for reference | | |

Test Items and Results

| Test Item | Result | Notes |
|---|---|---|
| Ginsenoside Rg1 | 155.40 mg/kg | |
| Ginsenoside Rg2 | 47.16 mg/kg | |
| Ginsenoside Rg3 | 2284.47 mg/kg | |
| Ginsenoside Rh1 | 0.00 mg/kg | |
| Ginsenoside Rh2 | 858.04 mg/kg | |
| Ginsenoside Rf | 12.56 mg/kg | |
| Crude saponin | 78.7 mg/g | |

Remarks: The content of the above test report is the test result of the materials submitted by the client and the Foundation is not liable for all matters which may be caused by the use rather then a test purpose.

August 12, 2011

Industry-University Collaboration Foundation of JOONGBU University

METHOD FOR PRODUCING CULTURED ROOT OF PURPLE GINSENG

CROSS-REFERENCE TO RELATED APPLICATION

This application claims the benefit of Korean Patent Application No. 10-2011-0020355, filed on Mar. 8, 2011 in the Korean Intellectual Property Office, Korean Patent Application No. 10-2011-0030577, filed on Apr. 4, 2011 in the Korean Intellectual Property Office, Korean Patent Application No. 10-2011-0085253, filed on Aug. 25, 2011 in the Korean Intellectual Property Office and Korean Patent Application No. 10-2011-0119040, filed on Nov. 15, 2011 in the Korean Intellectual Property Office, the disclosure of which is incorporated herein by reference.

TECHNICAL FIELD

The present invention relates to a novel method for processing a cultured root of wild ginseng for increasing a certain saponin content.

BACKGROUND

A wild ginseng, called as a scientific name of *Panax schinseng* NESS, is similar to a ginseng, but it is formed with a slightly different gene. The pharmacological effects of a wild ginseng are significantly superior to those of a ginseng, but due to its rarity there is a great limitation in the study and utilization thereof. However, recently, due to a development of cell culture techniques, a wild ginseng cell can be cultured to study or utilize the wild ginseng.

An effective ingredient of a wild ginseng is known as a ginsenoside and its main pharmacological effects are known to have numerous physiological activities including an immunological enhancement action, an antidiabetic action, a recovery from fatigue, an anti-stress action, a brain activity promotion effect, a nerve cell protection action, a blood circulation promotion action, a sexual dysfunction improvement action, a central nervous inhibitory action, a ditoxication effect, a platelet aggregation inhibitory action, particularly anticancer and cancer treatment.

On the other hand, when such a ginseng is processed, a ginsenoside content is mostly increased. A method for processing such a ginseng generally comprises repeatedly steaming and drying the ginseng several times under a high condition of over 100° C. However, in such cases, since the steaming and drying must be repeated several times and they must continuously satisfy with a complicated condition of preparation, they may bring about reduction in the productivity and economic efficiency of the preparation process. Further, there is a problem that a content of an effective ginsenoside ingredient contained in the processed ginseng is not substantially increased.

DISCLOSURE OF THE INVENTION

Technical Problem

Thus, the present invention has been designed in order to resolve the problems encountered with prior arts as mentioned above. The purpose of the present invention is to provide a novel method for producing a cultured root of purple wild ginseng which can process a cultured root of wild ginseng rather than a ginseng to obtain various kinds of ginsenoside ingredients in a high content.

Technical Solution

In order to accomplish the above mentioned purpose, the present invention provides a method for producing a cultured root of wild ginseng with an increased content of ginsenoside Rg3, Rh2, Rg2 and Rh1 which comprises a first step (i) of introducing a cultured root of dried wild ginseng or its powder in a closed high pressure steamer, adding thereto a water within a range of about 1/50~1/100 of the volume of container equipped in the steamer and then conducting a first heating at a temperature of 80~100° C. for 10~48 hours under a high pressure condition of 1.5~2 bar.

The production method according to the present invention further comprises a second step (ii) of conducting the heating and drying at a temperature of 100~500° C. for 10~48 hours in a state of maintaining the high pressure condition of the above first step (i).

The production method according to the present invention comprises, preferably, conducting the first step or the second step in a state of maintaining the condition of the step (i) and then 1~10 times repeatedly conducting the first step, the second step, or both the first and second steps.

Also, the present invention provides a method for producing a cultured root of wild ginseng with an increased content of ginsenoside Rg3, Rh2, Rg2 and Rh1 which comprises 1~10 times repeatedly conducting a second step (ii) of introducing a cultured root of dried wild ginseng or its powder in a closed high pressure steamer, adding thereto a water within a range of about 1/50~1/100 of the volume of a container equipped in the steaming machine and then heating and drying them at a temperature of 100~500° C. for 10~48 hours under a high pressure condition.

In the present invention, the high pressure steaming machine is preferably equipped with a safety pin of maintaining a pressure in order to prevent a damage of the container.

The cultured root of dried wild ginseng preferably has less than 5% of water content.

In the above first and second steps, a range of temperature, a volume of water added, and a range of high voltage are not limited to the above mentioned range and they can variously control depending on the desired use.

Furthermore, the present invention provides a cultured root of purple wild ginseng produced by the above mentioned method. The cultured root of wild ginseng prepared has as many as about 300 times more increased content of ginsenoside Rg3 as compared with a wild ginseng as shown in the attached tables and also can produce various kinds of ginsenoside ingredients in a large quantities by controlling the temperature and pressure.

Advantageous Effects

The present invention can increase productivity and economic efficiency of a wild ginseng by simplifying the production process and provide a novel method for processing a cultured root of purple wild ginseng with a significantly increased content of a certain ginsenside ingredient.

The cultured root of wild ginseng produced according to the present invention contains various kinds of saponin ingredients in a higher quantity, as compared with a cultured root of general wild ginseng or a cultured root of wild ginseng processed by a conventional method. Accordingly, when the above cultured root of wild ginseng or a supplementary health food containing the cultured root are taken, it is possible to show various pharmacological efficacies due to a high content of Rg2+Rh1 (brain function activation), Rg3 (cancer cell metastasis inhibitor) and Rh2 (cancer therapeutic agent) and the like.

BRIEF DESCRIPTION OF DRAWING

FIG. 2 shows an analysis and test report of ginsenoside ingredients of the cultured root of wild ginseng produced in Example 2.

FIG. 3 shows an analysis and test report of ginsenoside ingredients of the cultured root of wild ginseng produced in Example 3.

FIG. 4 shows an analysis and test report of ginsenoside ingredients of the cultured root of wild ginseng produced in Example 4.

BEST MODE FOR CARRYING OUT THE INVENTION

Figure 1:
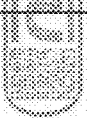
FIG. 1 shows an analysis and test report of ginsenoside ingredients of the cultured root of wild ginseng produced in Example 1.

Hereinafter, the present invention is described in more detail.

The method according to the present invention is characterized by processing a cultured rood of wild ginseng with a water vapor under high pressure and high heat, instead of several times repeatedly steaming and processing a conventional ginseng under an atmospheric pressure condition.

Through such processing, the present invention can significantly increase a content of a certain gensenoside (e.g., Rh1, Rg3, Rh2, etc.) by hydrolyzing a conventional ginsenoside (e.g., Rg1) contained in the cultured root of wild ginseng and then newly synthesizing effective ingredients of other ginsenoside using the decomposed gensenoside and the ingredients of cultured root itself (please refer to Table 1 and FIGS. 1 through 4).

In one embodiment of the novel method for producing the cultured root of wild ginseng according to the present invention, the cultured root of dried wild ginseng and water are introduced in a high pressure steaming machine, and then heated and dried while maintaining a high pressure state if possible. In a more preferred embodiment, the following three methods can be illustrated. However, the invention is not limited only to these methods.

1) First Embodiment

The first embodiment of the method for producing the cultured root of wild ginseng according to the present invention comprises introducing the cultured root of dried wild ginseng or its powder in a closed high pressure steaming machine, adding a water within a range of about 1/50~1/100 of the volume of a container equipped in the above steamer, and then conducting a first heating at a temperature of 80~100° C. for 10~48 hours under a high pressure of 1.5~2 bar.

The cultured roots of wild ginseng used in the present invention refer to cultured roots of ginseng produced by tissue-culturing a wild ginseng under a certain condition, but are not limited to these. The cultured roots of wild ginseng itself and the cultured roots of processed wild ginseng which are conventionally known in the art can be used, and these include a wild ginseng and a cultivated wild ginseng.

The ginseng origin used in the tissue cultivation of the cultured roots of wild ginseng is not particularly limited. As one example, the ginsengs which are originally from Korea, the United States, Japan, Himalaya, Vietnam and China can be used.

Non-limiting examples of the cultured roots of wild ginseng which can be used herein include a living body of a cultured root of wild ginseng, a powder of a cultured root of wild ginseng, a concentrate of a cultured root of wild ginseng and so on. In the present invention, the powder of the cultured root of wild ginseng is mainly used. In addition, any of a white ginseng, a fresh ginseng, a red ginseng and the like which are commercially available in the art can be used in the practice of the present invention.

When the cultured root of wild ginseng contains a large amount of moisture, it is difficult to pressurize the same under the above mentioned high pressure condition. Therefore, the cultured root of dried wild ginseng is preferred. As one example, the cultured root of dried wild ginseng has preferably less than 5% of moisture content.

Further, the amount of the cultured root of wild ginseng used is not particularly limited. As one example, it is preferable to use it within a range of less than 1/10 of the volume of the container.

In the present invention, the high pressure steaming machine refers to an equipment of adding a certain pressure condition and steaming a cultured root of wild ginseng. The high pressure steaming machine includes a container capable of receiving the cultured root of wild ginseng under a certain high pressure condition. Non-limiting examples of the container which can be used herein include a silver container, earthenware, a glass container, a ceramic container, a harmless metal container and the like. Using earthenware with high germanium content together is preferred.

Water used together with the cultured root of wild ginseng prevents from excessively increasing a water vapor pressure in a high pressure steaming machine, and the cultured root of wild ginseng dried in the container absorbs moisture. In view of these, water can be used within a range of 1/50 to 1/100 of the volume of the container in which the cultured root of wild ginseng is introduced. By controlling the heating temperature in a closed container, a pressure resulting from the water vapor pressure in the container can be controlled.

Further, in the first step, the pressurized condition in a high pressure steaming machine is not particularly limited. It is effective to use the maximum water vapor pressure which can be obtained by conducing the heating at the temperature of less than 100° C., preferably 80~95° C. Herein, it is necessary to equip a safety pin for preventing a damage of the high pressure steaming machine.

In the above first step, the heating and drying can be conducted at a temperature of less than 100° C., preferably 80~100° C., for 10~48 hours. In order to sufficiently obtain ginsenoside ingredients, it is preferable to conduct the heating for a possible long time and thus, these are not limited only to the above range. The heating at a temperature of less than 100° C. is for the purpose of sufficiently obtaining ginsenoside ingredients produced at a temperature of less than 100° C.

2) Second Embodiment

The second embodiment of the method for producing the cultured roots of wild ginseng according to the present invention comprises heating the cultured roots of wild ginseng under higher pressure and temperature condition as compared with the above mentioned first embodiment. A preferred example thereof comprises introducing the cultured root of dried wild ginseng or its powder in a closed high pressure steaming machine, adding a water within a range of about 1/50~1/100 of the volume of container equipped in the above steaming machine, and then conducting the heating at a temperature of more than 100° C. for 10~48 hours in a state of maintaining a high pressure condition (the second step).

The heating of the second embodiment can be conducted, for example, at a temperature of more 100° C., preferably 100~500° C., for 10~48 hours. In order to sufficiently obtain ginsenoside ingredients in the same manner as the first step, it is preferable to conduct the heating for a possible long time and thus, these are not limited only to the above range.

When the temperature in the closed high pressure steaming machine is raised to more than 100° C., the internal pressure of the steaming machine resulting from the water vapor pressure will also be significantly increased. As such, the decomposition of a conventional ginsenoside and the synthesis of new ginsenoside can be significantly increased due to such the high pressure water vapor. Since a pressure is increased in proportion to a temperature, the above mentioned high pressure range is not particularly limited. As one example, the high pressure range of the second embodiment is preferable that the pressure of the steam is increased as much as possible within a range capable of standing the container. Additionally, the production condition can be applied identically to the above mentioned first embodiment or it can be properly changed.

When the second embodiment is either first practiced or alone practiced, it may further comprise a third step (iii) of conducting the heating at a lower temperature range than the second embodiment, in a state of maintaining the high temperature/high pressure condition of the second embodiment (ii) As one example, the heating in the above third step can be conducted at a temperature of 90~110° C. for 10~48 hours.

3) Third Embodiment

The third embodiment of the method for producing the cultured roots of wild ginseng according to the present invention comprises sequentially conducting the first embodiment (first step) and the second embodiment (second step). As one example, after completion of the first step, the cultured roots of wild ginseng can be produced by conducting a second heating and drying in a state of maintaining a high pressure condition of the first step. Alternatively, after the first step or the second step has been conducted in a state of maintaining the condition of the first step (i), the cultured roots of wild ginseng can be produced by several times repeatedly conducting and drying the first step, the second step or both the first and the second steps.

As the repeating time is increased, the kinds of effective ginsenoside ingredients in the cultured root of wild ginseng and the content thereof are increased. Therefore, the repeating times or order of the above mentioned first and second steps may not be particularly limited. As one example, the repeating times may be 1 to 10 times.

In the first embodiment through the third embodiment according to the present invention, a temperature range, an amount of water added, and a pressure range are not limited to the above mentioned ranges. Even applying to the higher temperature and pressure than the above mentioned range during a condition of not damaging the container equipped in the high pressure steaming machine is included within the range of the present invention.

On the other hand, the present invention discloses about once practicing the first and the second steps. If necessary, the first and the second steps can be repeatedly conducted more than once, for example 1~10 times. Also, properly changing the order of the first and the second steps depending on the desired use is included within a range of the present invention.

After taking the production step as mentioned above, the cultured roots of wild ginseng show a deep purple color.

According to the present invention, when the content of saponin which is the main ingredient of the cultured root of wild ginseng, is raised to a maximum content, it is possible include much more kinds of saponin ingredients as compared with a conventional wild ginseng. The term "saponin" used in the present invention refers to ginsenoside, i.e., ginseng saponin, unless indicated otherwise. Saponin of the other plant can variably increase in the same manner.

Particularly, the cultured roots of wild ginseng produced according to the present invention show ginsenoside ingredients and content behaviors which are different from the cultured roots of conventional wild ginseng.

As one example, it can be identified that the cultured roots of conventional wild ginseng has a high content of ginsenoside Rg1, whereas the content of ginsenoside Rg3 and Rh2 is extremely low. In contrast, the cultured roots of wild ginseng processed according to the present invention do not substantially present the content of ginsenoside Rg1, and the contents of ginsenoside Rg3 and Rh2 are increased to hundreds of times, respectively (please refer to Table 1). These results show that ingredients contained in the cultured roots of wild ginseng and a conventional ginseng saponin can be hydrolyzed or synthesized through the novel production method according to the present invention to thereby increase a better quality of saponin such as new ginsenoside Rh1, Rg3, Rg2 and Rh2.

Accordingly, the cultured roots of wild ginseng produced according to the present invention are anticipated to be effectively used in the field of a platelet aggregation inhibitory action, a cancer cell growth inhibition, a cancer metastasis inhibitory action, an anticancer activity expansion of anticancer agent, an anti-allergic effect, an anti-inflammatory and cancer therapy, which show the efficacies of ginsenoside Rg3 and Rh2. The reason thereof is that mass production of Rg3 and Rh2 is possible.

The cultured roots of wild ginseng produced according to the present invention is condensed, decomposed, freeze-dried or vacuum-dried to make a powder, or can be taken in the form of a solution formed by precipitating them in a spirit. Or it can be used as an injection or in several other forms. Or the powder or solution may be added to medicine, food, health supplemental and so on.

The cultured roots of wild ginseng produced according to the present invention can be used as a medicine for anti-cancer, anti-inflammatory, or anti-allergic therapies.

When the cultured roots of wild ginseng produced according to the present invention are used as a medicine for anti-cancer, anti-inflammatory, or anti-allergic therapies, they may optionally further comprise conventional carriers, excipients or diluents known in the art.

Further, the cultured roots of wild ginseng produced according to the present invention can be used as a supplemental health food.

BEST MODE FOR CARRYING OUT INVENTION

Hereinafter, the present invention is described in more detail with reference to examples. However, the following examples are intended to illustrate the invention, and the scope of the invention is not limited to these examples. The examples can be properly corrected and modified by a person skilled in the art within the scope of the present invention.

Example 1

1-1. Drying of the Cultured Roots of Wild Ginseng

The cultured roots of wild ginseng were harvested and three times cleanly washed with water. They were laid with a thickness of 3~5 cm on a dry wicker tray. The wicker tray was placed on an automatic dryer. They are dried at a temperature of 80° C. for 9 hours and processed as a fine powder so that the moisture content is less than 5%.

1-2. Preparation of the Cultured Roots of Wild Ginseng 500 g of the cultured roots of wild ginseng dried in Example 1-1 were introduced in a pure silver container (10 l) equipped in a high pressure steaming machine to which water of about 1/100 of the container volume was added. A safety pin was equipped therein so that the hydrostatic pressure was not increased more than 2 bar. The first heating was then conducted at a temperature of 95° C. for 24 hours.

Subsequently, the temperature was raised to 130° C. in a state of maintaining the pressure and then the second heating was conducted for 24 hours. The cultured roots of heated wild ginseng were laid with a thickness of 1~2 cm on a wicker tray and then dried at a temperature of 90~100° C. for 10 hours so that a moisture content is less than 5%. The cultured roots of wild ginseng produced from the above procedure could be analyzed to obtain the results as shown in Table 1 below.

Examples 2 and 3

The cultured roots of wild ginseng shown in the test reports of FIGS. 2 and 3 were produced by conducting the same procedures as Example 1.

Example 4

The cultured roots of wild ginseng were produced in the same manner as Example 1 except that they were produced through the first heating and drying steps without the second heating step.

Experimental Example 1

Comparison of saponin ingredients of the cultured roots of wild ginseng and saponin ingredients of the cultured roots of steamed wild ginseng The ingredient analysis of the cultured roots of wild ginseng prepared in Examples 1 to 4 was conducted by the Life Science Research Center in Industry-University Collaboration Foundation, JOONGBU University (Food Sanitation Test Organization Designation No. 38 by the Korea Ministry of Food and Drug Safety). The analysis results of the cultured roots of wild ginseng prepared are shown in Table 1 below.

In Examples 1 to 3, the cultured roots of wild ginseng were heated and steamed under high temperature and high pressure conditions of the first and second steps. In Example 4, the cultured roots of wild ginseng were heated and steamed under a high temperature and high pressure of the first step by changing the conditions.

As shown in Table 1 below, the cultured roots of wild ginseng prepared in Examples 1 to 4 have various kinds of saponin ingredients in a high content as compared with the cultured roots of non-treated wild ginseng. Particularly, the cultured roots of wild ginseng prepared in Examples 1 to 3 under the high temperature and high pressure significantly increase the content of certain ginsenoside Rh1, Rg3, Rh2 and so on.

Accordingly, the novel method for producing the cultured roots of wild ginseng according to the present invention can be usefully applied to several fields which require various pharmacological effects.

TABLE 1

|  | Test items and results (mg/g) | | | | | | | Condition | |
| --- | --- | --- | --- | --- | --- | --- | --- | --- | --- |
|  | Rg1 | Rf | Rg2 | Rh1 | Rg3 | Rh2 | Crude saponin | 1st step | 2nd step |
| Example 1 cultured roots of wild ginseng | 0 | 0.205 | 0.046 | 0.251 | 6.42 | 1.787 | 50.10 | o | o |
| Example 2 cultured roots of wild ginseng | 0 | 0.119 | 0.192 | 0.262 | 4.07 | 1.233 | 65.1 | o | o |
| Example 3 cultured roots of wild ginseng | 0.045 | 0.047 | 0.104 | 0.134 | 4.77 | 3.466 | 96.5 | o | o |
| Example 4 cultured roots of wild ginseng | 0.155 | 0.012 | 0.047 | 0.00 | 2.28 | 0.658 | 78.7 | o | x |
| Non-treated cultured roots of wild ginseng | 0.82 | 0.27 | 0.28 | | 0.02 | 0.02 | 7.37 | x | X |

What is claimed is:

1. A method for producing a dry ginseng product having an increased content of ginsenoside Rg3, Rh2, Rg2 and Rh1 comprising the steps of:
   (i) introducing cultured dried ginseng or its powder into a container within a closed high-pressure steaming machine;
   (ii) adding water to the container in a range of about 1/50~1/100 of the volume of the container;
   (iii) conducting a first heating and pressurization, whereby the container is heated to a temperature of 80~100° C. while maintaining a high-pressure of 1.5~2 bar for 10~48 hours to obtain a heated pressurized ginseng product; and (iv) drying the heated pressurized ginseng product.

2. The method according to claim 1, further comprising conducting a second heating and pressurization step following step (iii), whereby the container is further heated to a temperature of 100~500° C. while maintaining a high-pressure of 1.5~2 bar for 10~48 hours.

3. The method according to claim 2, further comprising repeating the first and second heating and pressurization steps.

* * * * *